United States Patent
Imran

[19]

[11] Patent Number: 5,964,796
[45] Date of Patent: Oct. 12, 1999

[54] CATHETER ASSEMBLY, CATHETER AND MULTI-PORT INTRODUCER FOR USE THEREWITH

[75] Inventor: Mir A. Imran, Palo Alto, Calif.

[73] Assignee: Cardiac Pathways Corporation, Sunnyvale, Calif.

[21] Appl. No.: 09/140,194

[22] Filed: Aug. 25, 1998

Related U.S. Application Data

[62] Division of application No. 08/812,354, Mar. 4, 1997, which is a continuation of application No. 08/271,867, Jul. 7, 1994, Pat. No. 5,607,462, which is a continuation-in-part of application No. 08/126,314, Sep. 24, 1993, Pat. No. 5,342,295.

[51] Int. Cl.$^6$ ....................................................... A61N 1/00
[52] U.S. Cl. .......................... 607/122; 604/164; 604/264; 604/43
[58] Field of Search ................................ 604/43–45, 164, 604/170, 264, 280, 263; 600/374; 607/98, 99, 113, 122

[56] References Cited

U.S. PATENT DOCUMENTS

| | | | |
|---|---|---|---|
| 4,602,645 | 7/1986 | Barrington et al. ...................... | 128/786 |
| 4,637,388 | 1/1987 | Melendy ................................. | 128/786 |
| 4,670,009 | 6/1987 | Bullock .................................... | 604/96 |
| 4,671,291 | 6/1987 | Wilson .................................... | 128/786 |
| 4,699,147 | 10/1987 | Chilson et al. ......................... | 128/642 |
| 4,769,005 | 9/1988 | Ginsburg et al. ....................... | 604/642 |
| 4,807,626 | 2/1989 | McGirr .................................... | 128/328 |
| 4,808,157 | 2/1989 | Coombs ................................... | 605/44 |
| 4,813,930 | 3/1989 | Elliott ...................................... | 604/53 |
| 4,838,879 | 6/1989 | Tanabe et al. ............................ | 604/53 |
| 4,905,667 | 3/1990 | Foerster et al. .......................... | 128/53 |
| 4,920,980 | 5/1990 | Jackowski ................................ | 128/53 |
| 4,940,064 | 7/1990 | Desai ....................................... | 604/105 |
| 4,963,128 | 10/1990 | Daniel et al. ............................ | 600/105 |
| 5,059,177 | 10/1991 | Towne et al. ............................ | 604/96 |
| 5,078,714 | 1/1992 | Katims ..................................... | 604/96 |
| 5,135,599 | 8/1992 | Martin et al. ............................ | 156/96 |
| 5,149,330 | 9/1992 | Brightbill ................................. | 604/96 |
| 5,199,950 | 4/1993 | Schmitt et al. .......................... | 604/96 |
| 5,203,338 | 4/1993 | Jang ......................................... | 128/96 |
| 5,211,176 | 5/1993 | Ishiguro et al. ......................... | 128/96 |
| 5,215,527 | 6/1993 | Beck et al. ............................... | 604/96 |
| 5,236,417 | 8/1993 | Wallis ...................................... | 604/96 |
| 5,237,996 | 8/1993 | Waldman et al. ....................... | 128/642 |
| 5,255,679 | 10/1993 | Imran ....................................... | 128/642 |
| 5,292,305 | 3/1994 | Boudewign et al. .................... | 604/43 |
| 5,327,889 | 7/1994 | Imran ....................................... | 128/642 |
| 5,342,299 | 8/1994 | Snoke et al. ............................. | 604/95 |
| 5,354,266 | 10/1994 | Snoke ....................................... | 604/28 |
| 5,400,783 | 3/1995 | Pomeranz et al. ...................... | 128/642 |
| 5,471,982 | 12/1995 | Edwards et al. ......................... | 128/642 |

FOREIGN PATENT DOCUMENTS

2565491 12/1985 France .................................. 128/642

Primary Examiner—Wynn Wood Coggins
Assistant Examiner—Deborah Blyveis
Attorney, Agent, or Firm—Flehr Hohbach Test Albritton & Herbert LLP

[57] ABSTRACT

A assembly for use in performing a medical procedure within a region in a body of a patient having a vessel therein comprising a multi-port introducer adapted to be inserted into a vessel of the patient. The multi-port introducer includes an elongate body having proximal and distal extremities and has spaced-apart lumens extending from the proximal extremity toward the distal extremity. The elongate tubular body has ports therein at the proximal extremity in communication with the lumens and openings in the distal extremity in communication with the lumens. The elongate tubular body has a length so that it can extend from the exterior of the body to said region in the body. A plurality of catheters is provided. Each of the catheters is slidably disposed in a separate lumen in the multi-port introducer and has a distal extremity adapted to be disposed in the vessel of the patient.

12 Claims, 7 Drawing Sheets

CATHETER ASSEMBLY, CATHETER AND MULTI-PORT INTRODUCER FOR USE THEREWITH

This application is a divisional of pending application Ser. No. 08/812,354 filed Mar. 4, 1997; which is a continuation of application Ser. No. 08/271,867 filed Jul. 7, 1994, now U.S. Pat. No. 5,607,462, which is a continuation-in-part of application Ser. No. 08,126,314 filed Sep. 24, 1993, now U.S. Pat. No. 5,342,295.

This invention relates to a catheter assembly, catheter and multi-port introducer for use therewith and more particularly to a diagnostic catheter assembly for electrophysiology studies and diagnostic catheter and multi-port introducer for use therewith.

Heretofore electrophysiology diagnostic studies have been carried out in cath labs for the purpose of studying the electrical characteristics of the heart. Typically this is accomplished with diagnostic catheters of various configurations of electrodes at the distal extremities. These catheters are 6 or 7 French in size and during an electrophysiology study a three to four of such catheters are utilized and sometimes a maximum of five. These catheters are positioned inside the heart in various locations. To accomplish such studies, a physician typically has to make several incisions and utilize several introducers with hemostasis valves on the proximal ends of the same. When such catheters and introducers are removed, there remains four or five holes in the veins or artery of the patient which may cause major problems for the patients, as for example hematomas. Persistent bleeding is a problem because typically such patients have been heparinized. Thus it is often necessary to hold down physically the puncture sites for periods as great as 20 minutes before clotting occurs. There is therefore need for new and improved catheter and introducer for the same and a method which will greatly reduce the number of puncture sites to only one.

In general, it is an object of the present invention to provide a catheter assembly, catheter and multi-port introducer for use therewith so that only a single site is required.

Another object of the invention is to provide a catheter assembly, catheter, multi-port introducer and method which is particularly useful for making diagnostic electrophysiology studies.

Another object of the invention is to provide a catheter assembly of the above character which utilizes a plurality of small diameter catheters which are introduced through a single multi-port introducer.

Another object of the invention is to provide catheters of the above character which are small in size and which can be provided in different electrode configurations.

Another object of the invention is to provide a catheter of the above character in which the distal extremity can be steered.

Another object of the invention is to provide a multi-lumen introducer of the above character which can receive a plurality of catheters through its multi-ports.

Another object of the invention is to provide a catheter of the above character which has a distal extremity which is very flexible to ensure that it will not penetrate the endocardium of the heart.

Another object of the invention is to provide a catheter of the above character in which the distal extremity and proximal extremities of the catheters are marked so that one catheter can be distinguished from another.

Another object of the invention is to provide a multi-port introducer of the above character which can be relatively short and which is provided with an atraumatic distal extremity.

Another object of the invention is to provide a multi-port introducer of the above character which is relatively long and which has an atraumatic distal extremity so that it can be introduced into a vessel of the patient adjacent the heart.

Additional objects and features of the invention will appear from the following description which the preferred embodiments are set forth in detail in conjunction with the accompanying drawings.

In general, the catheter assembly of the present invention for performing a medical procedure on a body consists of an introducer adapted to be inserted into a vessel of the patient. The introducer is provided with a plurality of lumens extending therethrough and opening into an entrance port. A plurality of catheters having proximal and distal extremities are removably positioned within the plurality of lumens in the introducer and extend distally of the introducer and are adapted to have their distal extremities positioned in different locations within the patient.

Figure 1:
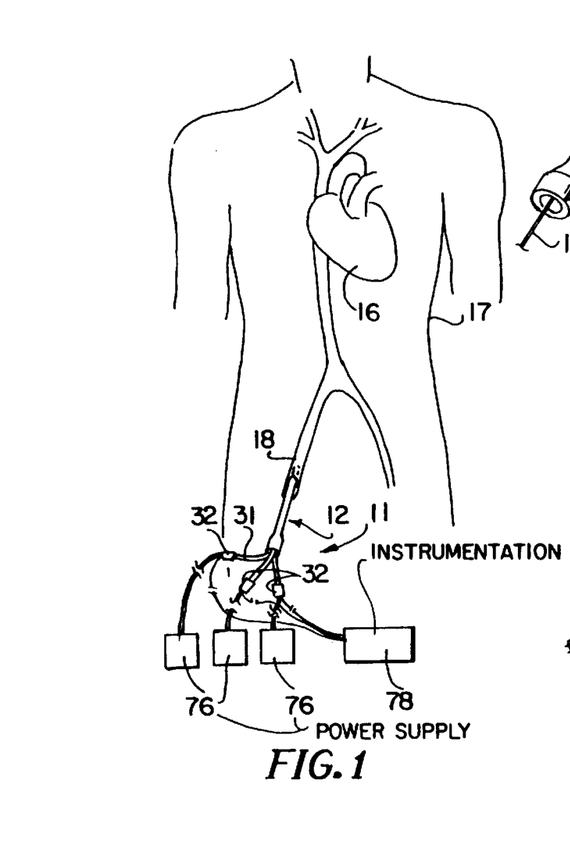
FIG. 1 is a schematic illustration showing the manner in which a catheter assembly and multi-port introducer of the present invention are introduced into the femoral vein and into the heart of a patient.

More in particular, as shown in the drawings, the catheter assembly 11 comprises a multi-port or multi-catheter introducer 12 and a plurality of catheters 13 which are introduced through the multi-port introducer 12. The catheter assembly 11 is shown being utilized in FIG. 1 in connection with diagnostic procedures, as for example electrophysiology studies of the heart 16 of a patient 17 introduced through a femoral vein 18 of the patient.

Figure 2:
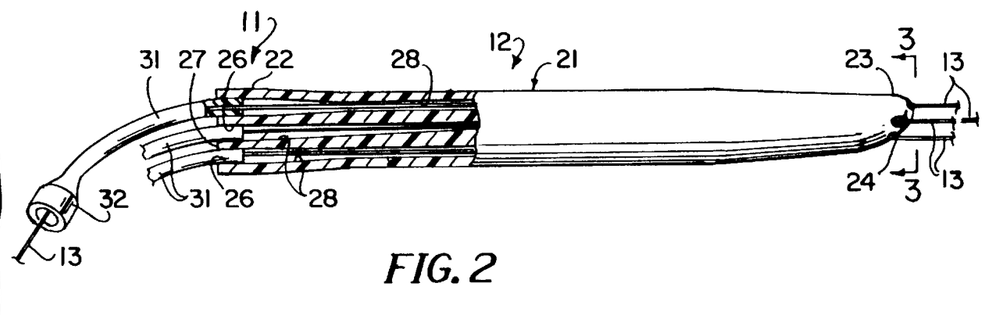
FIG. 2 is a side elevational view partially in cross section of the catheter assembly and the multi-port introducer shown in FIG. 1.

The multi-port introducer 12 as shown in FIG. 2 consists of an introducer body 21 having proximal and distal extremities 22 and 23. The body 21 is formed of a suitable material such as a medical grade plastic and can be relatively flexible. The introducer 12 can be of a suitable size, as for example 6 or 7 French ranging from 0.080 to 0.093 inches in diameter. The distal extremity 23 is provided with a rounded slightly tapered end 24 to provide an atraumatic tip for the introducer 12. The proximal extremity 22 is enlarged and is provided with a plurality of ports 26 spaced circumferentially around an end wall 27, as for example four or more ports. The ports 26 open into lumens 28 which extend longitudinally of the body 21 and which open through openings 29 in the rounded tapered end 24. Because of the tapering of the end 24, the openings 29 have generally an oval-shaped configuration even though the lumens 28 are circular in cross section. The lumens 28 can have a suitable size which can accommodate the catheters 13 which are to be inserted therethrough. Thus, by way of example if the catheters are of a 2 French size, the lumens 28 should have a slightly greater size so that they can be introduced through the lumens with relatively little friction.

As shown in FIG. 2, a plurality of tubular members 31 are bonded to the proximal extremity 22 of the body 21 and are in registration with the ports 26 so that the ports 26 are in communication with the tubular members 31. Hemostases valves 32 of a conventional type are mounted on and carried by the tubular members 31. They are sized so that they can accommodate the 2 French catheters 13 and form a seal therewith when the 2 French catheters are introduced through the introducer 12 as hereinafter described. It should be appreciated that if desired, hemostases valves 32 can be incorporated in the proximal extremity 22 of the introducer body 21 and the tubular members 31 eliminated.

Figures 3, 4:
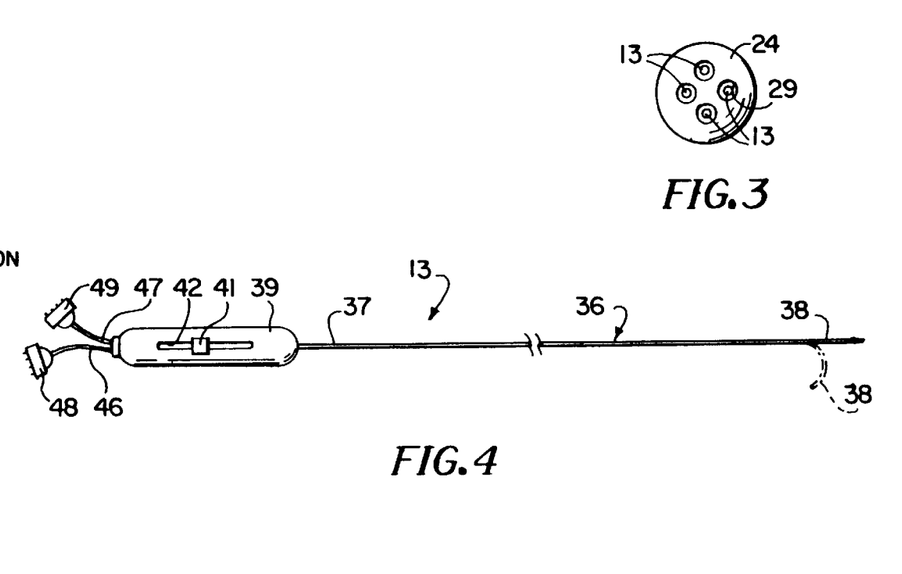
FIG. 3 is an end elevational view taken along the line 3–3 of FIG. 2.
FIG. 4 is a side elevational view of a catheter incorporating the present invention.

A catheter 13 utilized in the multi-port introducer 12 is shown in FIG. 4 and as shown therein consists of a flexible elongate member 36 which is provided with proximal and distal extremities 37 and 38. A handle 39 is secured to the proximal extremity 37 and includes a slider 41 which is slidably mounted in a slot 42 provided in the handle. The slider 41 controls means utilized for causing bending of the distal extremity 38. The handle is connected to first and second electrical cords 46 and 47 which are connected to plugs 48 and 49 that are utilized for a purpose hereinafter described. The distal extremity 38 can be bent in a conventional manner by the use of steering wires actuated by the slider 41 or alternatively by electrically energized Nitinol elements as described in U.S. Pat. No. 5,238,005, issued Aug. 24, 1993.

Figure 5:
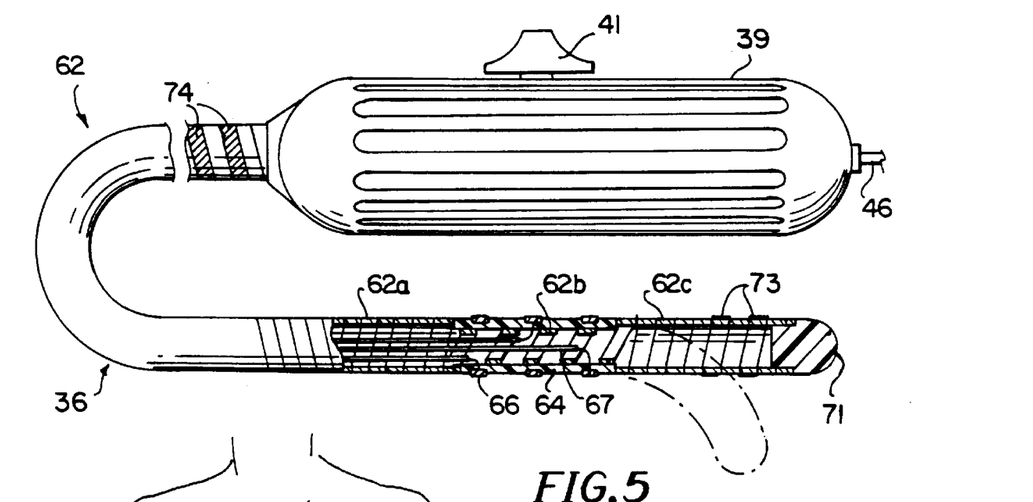
FIG. 5 is a side elevational view partially in cross section of the catheter shown in FIG. 4.

The flexible elongate member 36 is comprised of a tubular member 61 formed of a suitable material such as stainless steel and having a suitable diameter, as for example 2 French of approximately 0.026 inches in diameter.

It is desirable that the distal extremity 38 be very flexible and for that reason it is formed of a helical coil 62 which is flexible and hollow. The coil 62 can be formed of a suitable material such as a flat metal ribbon. Also, if desired, it can be formed of a radiopaque material such as a tungsten platinum alloy or palladium.

The coil 62 can have a suitable length, as for example 20–30 centimeters and can be formed of flattened round wire as shown. At the very distal extremity of the coil, the coil 62 is provided with an initial portion 62a having approximately the same diameter of the tubular member 61 for a length from 10–20 centimeters which is followed distally by step down portion 62b of a smaller diameter which can be accomplished by utilizing a mandrel having the two different diameters with the portion 62b having suitable length, as for example 1–2 centimeters.

A tube 64 formed of a suitable insulating material, as for example shrink tubing formed of plastic is placed over the portion 62b. A plurality of electrodes 66 formed of a suitable material such as platinum are provided in longitudinally spaced-apart positions on the tube 64. The electrodes 66 are connected by insulated conductors 67 that extend interiorly of the coil 62 to the proximal extremity of the flexible elongate member 36 and are connected through the handle 39 to the cord 47 and the connector 49.

The last 5–10 millimeter portion 62a of the distal extremity of the coil 62 is of a larger diameter, as for example the same diameter as the portion 62a. In order to impart greater flexibility to this portion 62c, the coils are spaced-apart with each coil having a diameter ranging from 0.016 to 0.018 inches a thickness of 0.002 to 0.003 inches and a spacing therebetween ranging from 0.004 to 0.006 inches.

A rounded tip 71 is provided in the distal extremity of the portion 62c and is formed of a suitable material such as a platinum tungsten alloy or palladium. A marker 73 is carried by the distal extremity of the catheter 13 to identify the catheter. Such identifying markers 73 can be formed as a bond as shown of a suitable radiopaque material such as a tungsten platinum alloy or palladium. Thus, by way of example if four of the catheters 13 are to be utilized in connection with the introducer 12, the catheters can be coded or marked in such a manner that each is provided with the same marking on the proximal end distal extremities. Thus, for example two bonds 73 can be provided on the distal extremity and similarly two markers 74 visible to the human eye such as colored markers can be provided on the proximal extremity.

In connection with the present invention, the two French catheters 13 can be designed to have the same mechanical characteristics, as for example a conventional 6 or 7 French size catheter. Thus the tubular member 61 can be formed in such a manner so as to provide good torquability characteristics whereby when the proximal extremity 37 is rotated, the distal extremity will rotate in a one-for-one relationship. The tubular member 61 can be formed in a conventional manner to achieve the desired stiffness and torque transfer capabilities desired. Preformed bends can be placed in the distal extremity 38 of the flexible elongate member 36 by forming the catheter 13 in a suitable manner. For example, the catheter 13 can be provided in a desired preformed shape which is assumed as soon as there is space for the distal extremity 38 to curve, as for example, as shown in broken lines in FIG. 4.

Conventional alternative steering means can be provided in which pull wires (not shown) are utilized controlled by actuation of the slider 41 or other appropriate mechanism. Similarly, Nitinol elements can be mounted in the distal extremity and can be electrically actuated by the slider 41 to accomplish the desired bending.

Operation and use of the catheter assembly 11 may now be briefly described as follows. Let it be assumed that the patient has been prepared for an electrophysiology study of the heart. The physician then makes the venous puncture in the femoral vein 18 of the patient. The introducer 12 is then introduced into the vein and the sutures as needed are placed around the puncture to prevent blood from leaking through the puncture. The hemostasis valves 32 provided in the multi-port introducer 12 are in a normally closed position to prevent blood from flowing therethrough. Catheters 13 are then introduced one by one through appropriate ports 26 through the hemostasis valves 32 to pass through the lumens 28 into the venous vessel 18 and then are advanced into appropriate locations in the venous side of the heart. As explained previously, this can be accomplished by utilizing catheters having preformed bends in the distal extremities or by steering the distal extremities utilizing the slider 41 on the handle 49 to either control the distal extremity by tensioning the pull wires or alternatively to supply energy to Nitinol elements disposed in the distal extremity. This latter approach is shown schematically in FIG. 1 in which a controller and power supply 76 is provided for each of the catheters 13. This controller and power supply can be provided in the handle 39 and be controlled by the slider 41. The signal outputs which are being measured by the electrodes 66 carried by the distal extremity of the catheters 13 can be viewed on instrumentation 78 connected to the connectors 48 connected to the handle 39 of each of the catheters 13.

During medical procedures, as for example an EP study, the physician can view the distal extremities of the catheters 13 by viewing the same under fluoroscopy and then can move the proximal extremities by movement of the handles. By observing the markings on the distal extremities of the catheters, the physician can associate a marking with a marking provided on the proximal extremity so that he can move the catheter he desires to move. Thus, the physician can advance or retract the distal extremity of the catheter by grasping on the handle 39. Also the physician can rotate the catheter by rotation of the handle 39. Bending can be accomplished by moving of the slider 41 on the handle 39.

After the medical procedure has been accomplished, as for example, the EP study has been completed, the catheters 13 can be removed one by one from the multi-port introducer 12 after which the multi-port introducer can be removed. Alternatively, the multi-port introducer 12 and the catheters 13 carried thereby can be removed as a unit. After the multi-port introducer 12 has been removed, the incision through which the introducer has been introduced can be closed in a conventional manner. It can be seen that with the catheter assembly 11 of the present invention and the method herein disclosed it is only necessary to make a single incision at a single site, into the patient while permitting multiple catheters to be introduced into the patient from this same site. This greatly decreases bleeding which may occur and minimizes the possibilities of the occurrence of hematomas.

Figures 6, 7:
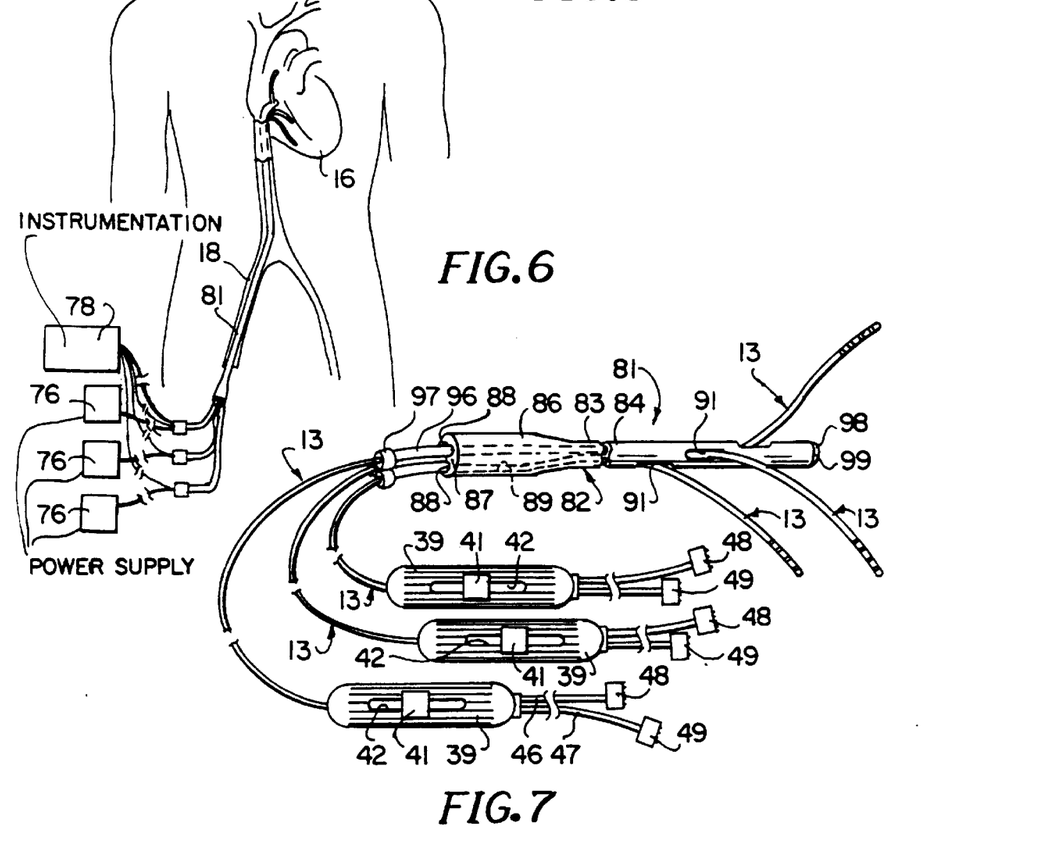
FIG. 6 is a schematic illustration showing the use of another catheter assembly and a long multi-port introducer incorporating the present invention.
FIG. 7 is a side elevational view of the catheter assembly and the long multi-port introducer shown in FIG. 6.

In certain medical procedures utilized in the present invention may be desirable to provide a long multi-port introducer 81 which as shown schematically in FIG. 6 can again be introduced through the femoral vein 18 with the introducer having a length so that its distal extremity can be positioned near the opening to the right atrium of the heart at the junction of the superior and inferior vena cavas. A side elevational view of the long multi-port introducer 81 is shown in FIG. 7 with a plurality of catheters 13 of the type hereinbefore described disposed therein. The introducer 81 is provided with a body 82 generally of the same diameter as the body 21 of the multi-port introducer 12 and can have a suitable size, as for example 6–7 French. It is provided with proximal and distal extremities 83 and 84 and can have a suitable length, as for example 30–70 centimeters. The body 82 can be formed of a suitable material such as plastic. It is provided within a large head 86 formed integral with the proximal extremity 83 and is provided with a wall 87 having a plurality of spaced-apart ports 88 therein which open into lumens 89 that are in communication with staggered openings 91 provided in the distal extremity 84. The ports 88, the lumens 89 and the openings 91 are sized so that they can accommodate the catheters 13. Thus, by way of example if the catheters 13 are of the 2 French size the ports 88, the lumens 89 and the openings 91 should be of a size which is slightly greater than that to permit easy slidable movement of the catheters 13 within the introducer 81. Tubular members 96 are connected into the ports 88 and are provided with hemostatic valves 97 on their proximal extremities which are adapted to receive the catheters 13.

The openings 91 have been staggered on the distal extremity 84 to reduce the possibility of stasis in the blood which could potentially cause emboli. The distal extremity 84 has been provided with an atraumatic tip 98 similar to that hereinbefore described for the introducer 12. Thus, it can be seen that the openings 91 are positioned proximally of the tip 98 rather than having the openings be in the tip 24 as with the introducer 12 hereinbefore described. With a short introducer 12, it is more difficult to place the openings in the side of the introducer because there is a tendency for a catheter when it leaves the openings to turn on its axis making it difficult to form a sharp bend in the catheter. With the long introducer 81, this is less of a problem because the tip 93 can be positioned so that the catheters 13 can be readily positioned. A radiopaque material 99 can be provided on the tip 98 so that the tip can be visualized fluoroscopically.

Operation and use of the long introducer 81 in connection with the catheters 13 is similar to that hereinbefore described with the principal difference being that the long multi-port introducer 81 is positioned so that its tip is near the opening of the right atrium of the heart as hereinbefore described. Thereafter, the catheters 13 can be deployed and manipulated in the same manner as hereinbefore described to accomplish the desired medical procedures. After the desired medical procedure, as for example, an electrophysiology study has been completed, the catheters 13 can be removed after which the introducer 81 can be removed and the puncture site closed in a conventional manner.

Another embodiment of a catheter assembly 101 incorporating the present invention is shown in FIGS. 8–11 which utilizes a very short introducer that is adapted to receive the catheter assembly 101 and consists of a flexible elongate member 102 having proximal and distal extremities 103 and 104. The flexible elongate member 102 is formed of a suitable material such as plastic and is provided with a plurality of lumens, as for example four lumens 106, 107, 108 and 109 (see FIG. 9) extending from the proximal extremity 103 to the distal extremity 104. The lumens 107, 108 and 109 exit through the side parts 111, 112 and 113 of the flexible elongate member 102 adjacent the distal extremity in spaced-apart positions for a purpose hereinafter described. The distal extremity 104 is provided with a tip electrode 116 and a ring electrode 117 spaced proximally of the tip electrode and are insulated from each other. The tip electrode and the ring electrode 117 are connected by leads 118 and 119 which extend through the lumen 106 to the proximal extremity and are connected to an electrical connector 121.

Figures 8, 9:
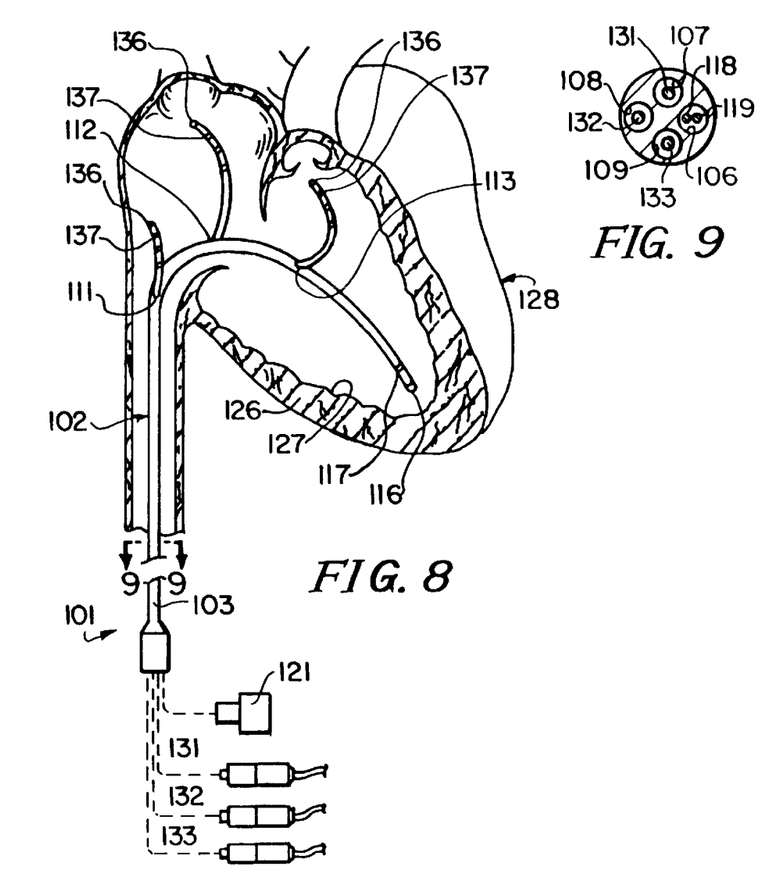
FIG. 8 is another schematic illustration showing the use of another embodiment of a catheter assembly and a multi-port introducer incorporating the present invention.
FIG. 9 is a cross-sectional view taken along the line 9—9 of FIG. 8.

The flexible elongate member 102 as described can comprise a catheter of a suitable size, as for example 7 French which can be utilized for sensing a signal in the wall 126 a chamber, forming the right ventricle 127 in a heart 128. With a flexible elongate member 102 of this size, it can serve as the catheter which can be also utilized for introducing smaller size catheters into the right ventricle. Thus, by way of example, three additional catheters 131, 132 and 133 can be provided of a suitable size, as for example 2 French which can be introduced into the lumens 107, 108 and 109. Each of the catheters 131, 132 and 133 can be constructed in the manner hereinbefore described and can be provided with tip electrodes 136 and a plurality of longitudinally spaced-apart ring electrodes 137. The 2 French catheters 131, 132 and 133 can be advanced through their respective side ports 111, 112 and 113 and moved into engagement with different portions of the wall of the heart as shown in FIG. 8. They can be utilized to make a conventional electrophysiology study using the signals from the right atrium and the right ventricle of the heart 128. The 7 French catheter formed by the flexible elongate member 102 as well as the catheters 131, 132 and 133 need not necessarily be steerable, however, it should be appreciated that if steerability is desired, that feature can be readily provided in the catheters. In order to eliminate the need for steerability, the 2 French catheters which are utilized in the larger 7 French catheter 102 can have preformed bends, as for example those shown in FIGS. 10 and 11.

From the foregoing construction of the catheter assembly 101 it can be seen that the large 7 French catheter 102 can either be considered to be a multi-port introducer which has electrodes carried by the distal extremity and which can be positioned in the right ventricle of the heart for mapping signals in one area of the heart and that the other smaller 2 French catheters 131, 132 and 133 can be used for mapping other areas of the heart.

As can be seen by utilizing catheters 131, 132 and 133 which have been provided with steering capabilities in the manner hereinbefore described or which have been provided with preformed bends, it is still possible to perform a conventional electrophysiology study from a single puncture site by with as few as three additional catheters in addition to the flexible elongate member 102 which also serves as a multi-port introducer with its own mapping capabilities.

Figure 9A:
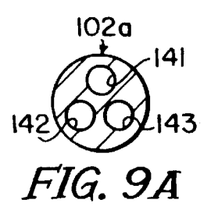
FIGS. 9A, 9B and 9C are cross-sectional views similar to FIG. 9 showing additional embodiments of multi-port introducers incorporating the present invention.
Figure 9B:
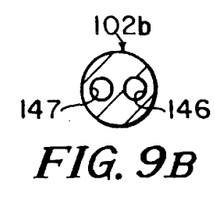
Figure 9C:
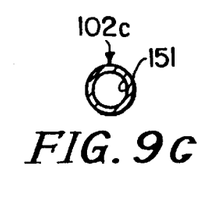
Figures 10, 11:
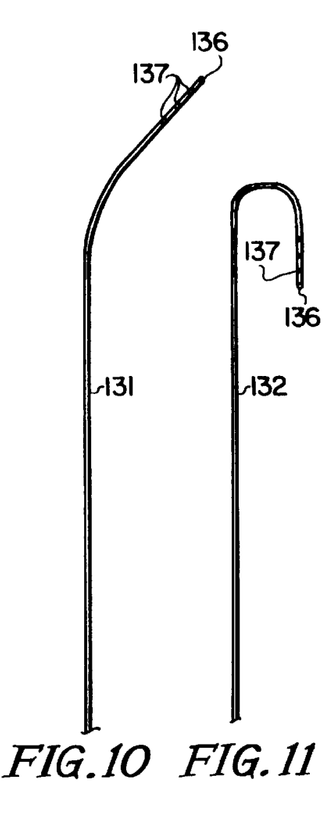
FIG. 10 is a partial side-elevational view of the distal extremity of a catheter incorporating the present invention having one type of bend formed in the distal extremity thereof.
FIG. 11 is another partial side-elevational view of a catheter incorporating the present invention having a different bend therein.

It should be appreciated that in connection with the present invention when it is desirable to have a smaller size introducer with fewer catheters, as for example in pediatric applications, arrangements such as that shown in FIGS. 9A, 9B and 9C can be utilized to provide catheter assemblies of smaller diameter. Thus, with the 7 French catheter assembly having four lumens, the outside diameter is approximately 0.092". For a smaller catheter assembly where only three lumens 141, 142 and 143 in the flexible elongate member 102a, the diameter can be reduced to approximately 0.080". When a still smaller diameter is desired, the outside diameter of the flexible elongate member 102b can be still further reduced by only providing two lumens 146 and 147 which can slidably receive 2 French catheters of a type hereinbefore described, the diameter can be reduced to 0.070". With only a single lumen 151 in a flexible elongate member 102c, the diameter can be reduced to 0.040". In these embodiments shown in FIGS. 9A, 9B and 9C all of the lumens have an inside diameter of 0.030".

Although this concept of utilizing fewer lumens and fewer 2 French catheters to make possible a smaller multi-port introducer is set forth with respect to the catheter assembly shown in FIG. 8, it should be appreciated that this concept can be used with respect to the embodiments heretofore described. The principal advantage to this approach is that it reduces the number of catheters required by utilizing the introducer itself as one of the catheters.

Figure 12:
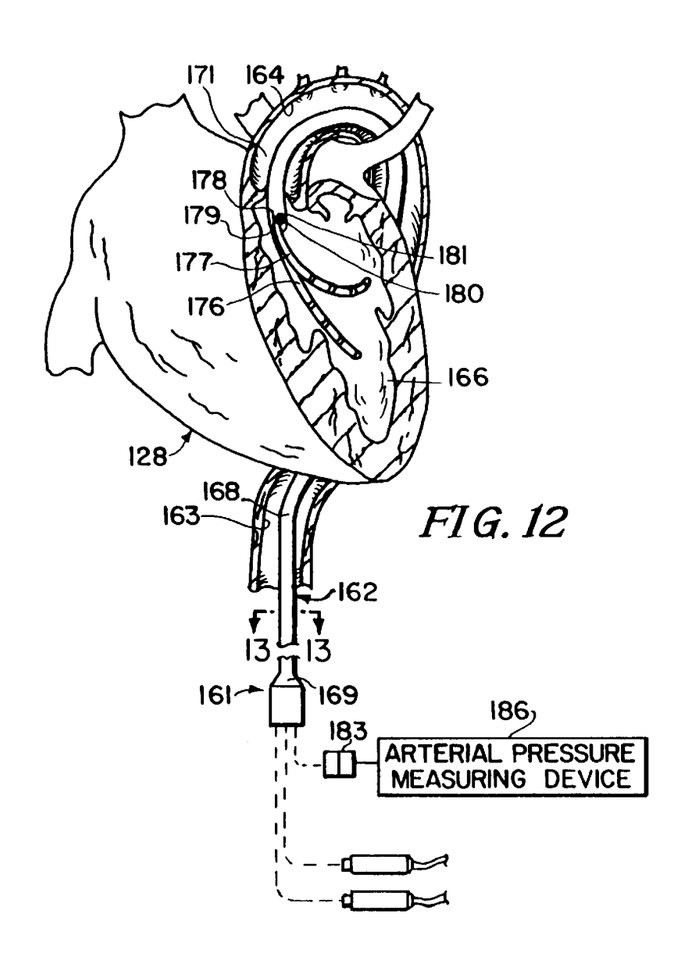
FIG. 12 there is shown another schematic illustration showing the use of another embodiment of a catheter assembly and multi-port introducer incorporating the present invention.
Figure 13:
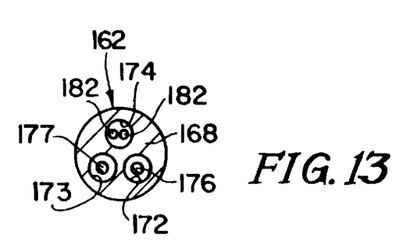
FIG. 13 is a cross-sectional view taken along the line 13—13 of FIG. 12.

In FIGS. 12 and 13, there is shown another embodiment of a catheter assembly 161 and a multi-port introducer 162. The multi-port introducer 162 is introduced through the femoral artery 163 into the aorta 164 and into the left ventricle 166 of the heart 128. The multi-port introducer 162 is comprised of a flexible elongate member 168 having proximal and distal extremities 169 and 171. By way of example, as shown in FIG. 13, the flexible elongate member 168 can be provided with lumens 172, 173 and 174 extending between the proximal and distal extremities 169 and 171. The lumens 172, 173 and 174 can be sized in the manner hereinbefore described and can accommodate mapping and/or ablation catheters 176 and 177 which are introduced therethrough into the lumens 172, 173 and which exit through end ports 178 and 179 provided in the distal extremity 171 of the flexible elongate member 168. Another port 180 can be utilized for carrying a pressure transducer 181 connected by wires 182 to a connector assembly 183 which is connected into a arterial pressure measuring device 186 of a conventional type. The proximal extremities of the catheters 176 and 171 are connected to connectors 188 and 189.

Thus, it can be seen with such a catheter assembly 161 and multi-port introducer 162 it is possible to perform mapping and ablation in the left ventricle at the same time to measure the pressure in the left ventricle. The measurement of arterial pressure during electrophysiology studies is desirable because it has been found that such electrophysiology studies frequently induce tachycardia. A radical drop in arterial pressure indicates immediately that heart failure is occurring thereby making it possible to determine how long tachycardia can be tolerated by the patient.

Figure 13A:
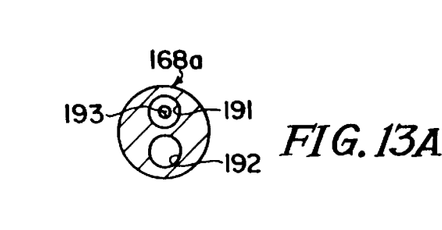
FIG. 13A is a cross-sectional view similar to FIG. 13 showing a smaller multi-port introducer.

When it is desired to provide a smaller multi-port introducer 162, an arrangement such as shown in FIG. 13A can be utilized in which the flexible elongate member 168a is provided with only two lumens 191 and 192 in which lumen 191 can be utilized for receiving an ablation catheter 193 and the lumen 192 can be utilized for measuring arterial pressure.

In connection with the present invention, although the small catheters have been discussed as being of the 2 French size it should be appreciated if desired even smaller catheters can be provided, as for example 1½ or 1 French or larger catheters, as for example 2½ or 3 French size ablation catheters.

Although the present invention has also been described principally in connection with making electrophysiology measurements in the heart, it should be appreciated that the present concept of utilizing a multi-port introducer to reduce the number of incisions in a patient is not limited to mapping and ablation procedures but also can be utilized for introducing ablation catheters, catheters for measuring blood pressure and the like.

Figures 14, 15:
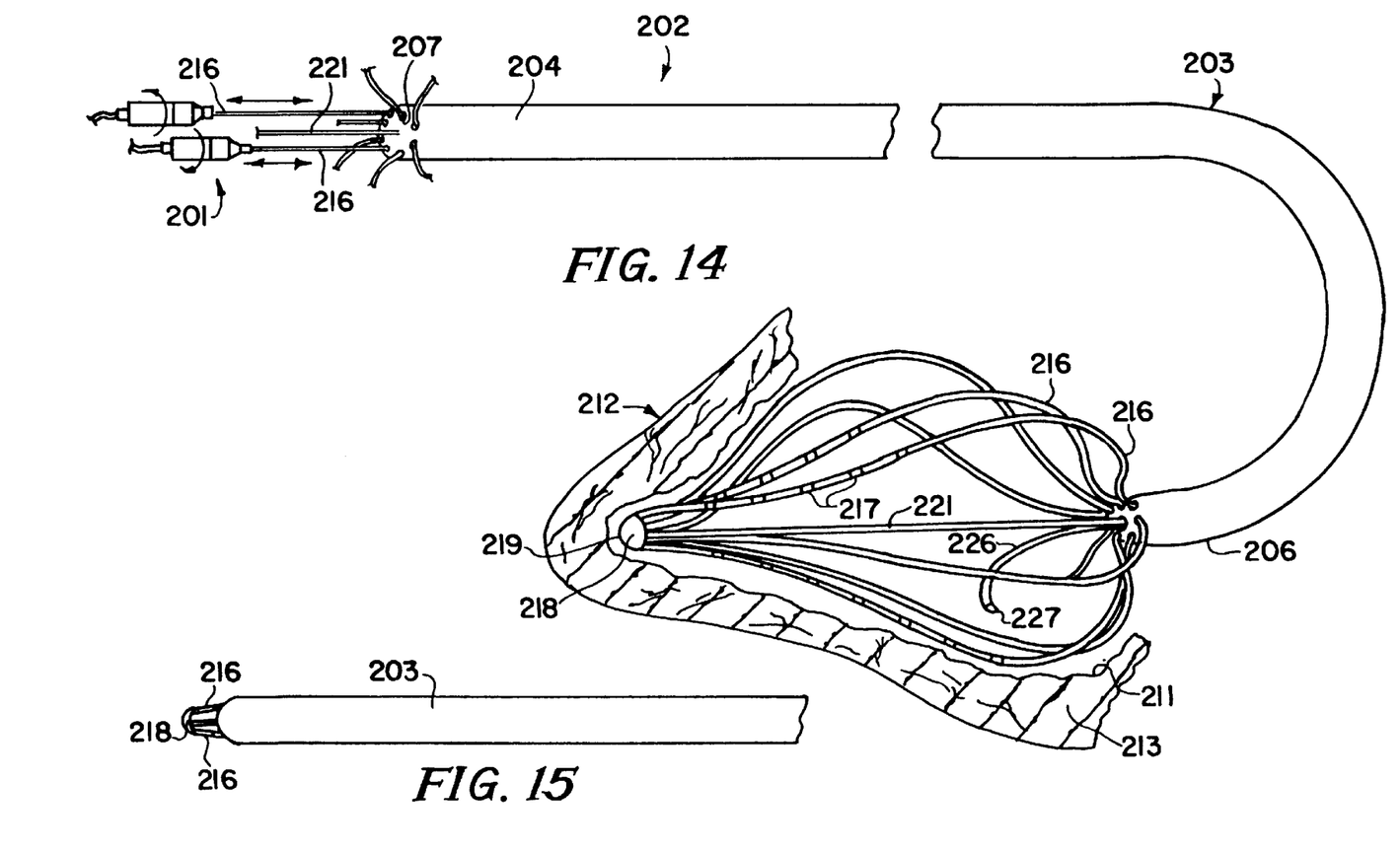
FIG. 14 is another schematic illustration showing the use of another embodiment of a catheter assembly and introducer incorporating another embodiment of the present invention.
FIG. 15 is a partial end-elevational view of the distal extremity of the catheter assembly and introducer with the catheter assembly retracted into the introducer.
Figures 16, 17, 18:
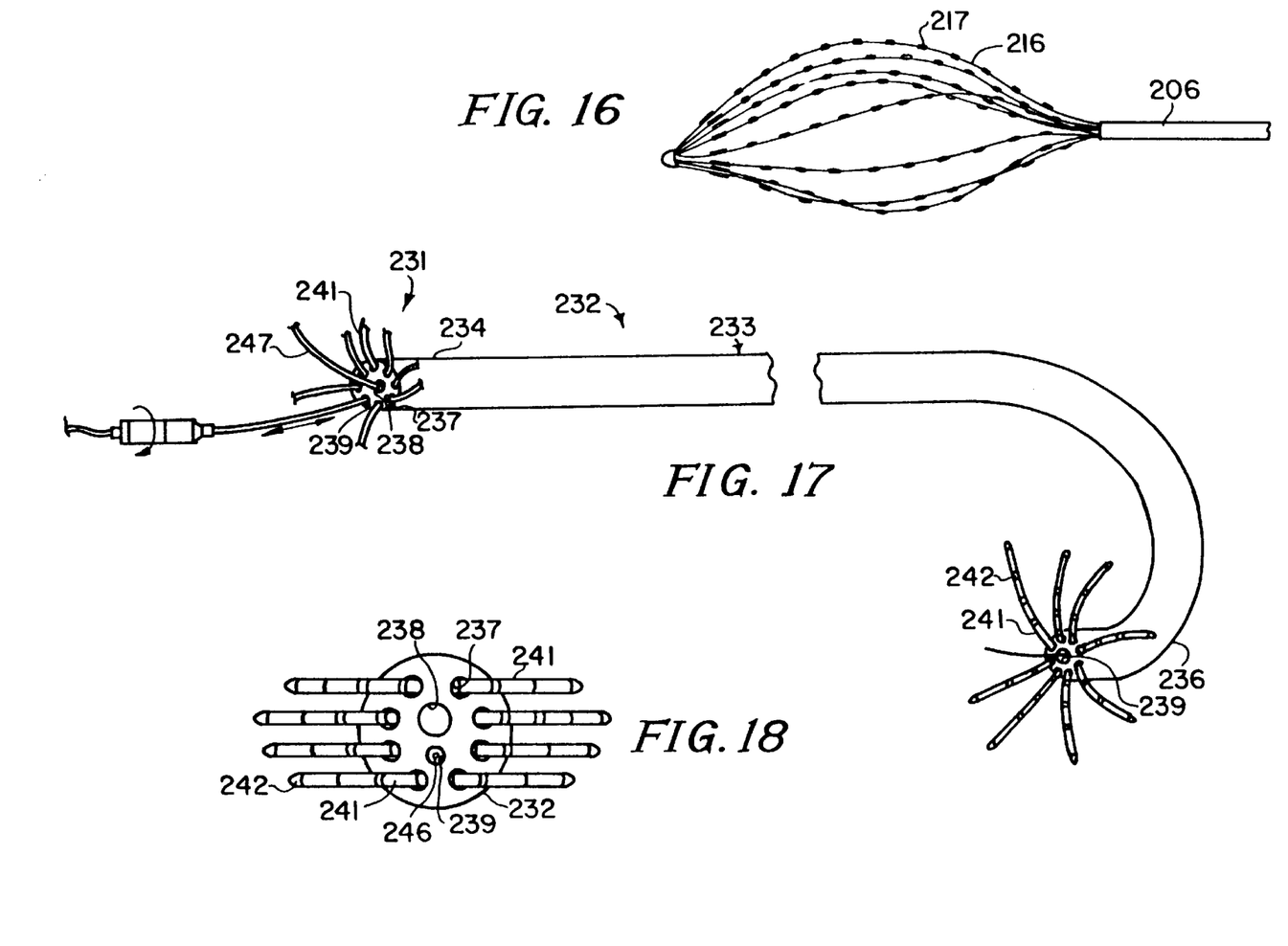
FIG. 16 is an isometric view showing the manner in which the catheter assembly shown in FIG. 14 can be deployed.
FIG. 17 is a schematic illustration of another embodiment of a catheter assembly and multi-port introducer incorporating the present invention.
FIG. 18 is an end elevational view showing another arrangement for the catheters as they are deployed from the distal extremity of the multi-port introducer.

Still another embodiment of the invention is shown in FIGS. 14, 15 and 16 which show a catheter assembly 201 used with a multi-port introducer 202 of the present invention. The multi-port introducer 202 consists of a flexible elongate member 203 having proximal and distal extremities 204 and 206. The flexible elongate member 203 is formed of a suitable medical grade plastic and can have a size ranging from 7 to 8½ French. It is provided with a plurality of circumferentially-spaced lumens 207 surrounding a central lumen 208 all which extend from the proximal extremity 204 to the distal extremity 206. The flexible elongate member 203 has a length so that it can extend from outside the body through the femoral artery into the left ventricle of the heart 212 or from the femoral vein to the right atrium or ventricle.

In accordance with the present invention, a plurality of small size catheters 216 can be provided in the lumens 207 and can be of the type and size hereinbefore described and can range from 1 to 4 French, and preferably 2 French, for example the small size catheter 13 as shown in FIG. 4. The distal extremities of the catheters 216 are provided with a plurality of electrodes 217 which are spaced apart axially of the catheters shown in FIG. 1. The electrodes 217 are connected by conductors or wires (not shown) to the proximal extremity of the catheters and are connected to the electrical connectors 48 and 49 hereinbefore described in conjunction with FIG. 4. The ends of the distal extremities of the catheter 216 are connected to an end cap 218 which is provided with a rounded outer surface 219. Thus it can be seen that the distal extremities of the catheter 16 are interconnected so that they can be formed into a basket-like construction as shown in FIG. 14.

Operation and use of the catheter assembly 201 with the multi-port introducer 202 can now be briefly described in conjunction with FIGS. 14–16. Let it be assumed that the small size catheters 216 have been withdrawn so that the cap 218 is at the distal extremity of the multi-port introducer 202 as shown in FIG. 15 with the rounded surface 219 protruding therefrom. In this condition, the introducer 202 can be introduced into a femoral artery of a patient through a guiding catheter if that is deemed appropriate until the distal extremity has been advanced into the left ventricle 211 of the heart 212 having a wall 213. As soon as this has been accomplished, the small catheters 216 can be pushed in the lumens 207 since they are slidably mounted therein so that the distal extremities thereof advance out of the distal extremity 206 of the multi-port introducer 202.

Thus, as shown in FIG. 14, the catheters 216 can be pushed until the rounded surface 219 is in engagement with the apex of the left ventricle and thereafter they can be further pushed to cause them to flow outwardly to engage the side wall of the heart forming the left ventricle to move the electrodes 217 into engagement with the wall of the heart. By utilizing such a construction it can be seen that left ventricles, as for example diseased hearts which may be misshapen or of greatly different sizes can be accommodated by this construction merely by pushing inwardly on individual catheters 216 until they are in engagement with the wall 213 of the heart 212. By observing such a position fluoroscopically, it is possible if necessary to torque each of the catheters independently so that the distal extremities are spaced in the desired manner with respect to each other, as for example equal spacing when that is desired. After the desired mapping has been carried out and a region of interest has been found, it may be desirable to reposition the catheters 216 so that they are spaced closer together in the area of interest, as for example as shown in FIG. 16 to provide a finer resolution to more accurately locate the area of interest, as for example an area which may be causing the arrhythmia that is occurring in the heart. Thus, in this manner it is possible to provide much higher resolution mapping.

It should be appreciated that if desired, a pull wire 221 can be provided which extends through the central lumen 208 provided in the multi-port introducer 202. By use of such pull wires it is possible to provide small size catheter 216 which have distal ends which are pre-shaped into a desired bow or can have a straight shape. The pull wire 221 can be utilized to form the basket without providing undue pressure on the wall 212 forming the apex of the left ventricle.

When the mapping has been completed and it is desired to carry out an ablation, a second steerable ablation catheter 226 of the type described in co-pending application Ser. No. 07/894,529 filed Jun. 15, 1992, now U.S. Pat. No. 5,324,284 can be introduced through the central lumen 208 alongside the guide wire 221 to perform an ablation in a manner hereinbefore described. The ablation catheter 226 is provided with an ablation electrode 227 on its distal extremity which is adapted to be moved into engagement with the wall of the heart to perform an ablation in a manner hereinbefore described.

Still another embodiment of the invention is shown in FIG. 17 which consists of a catheter assembly 231 and a multi-port introducer 232. The multi-port introducer 232 is of the type hereinbefore described and is formed of flexible elongate member 233 having proximal and distal extremities 234 and 236. It is provided with a plurality of circumferentially spaced-apart lumens 237 extending from the proximal extremity to the distal extremity and a central lumen 238 extending in the same manner. It is also provided with another small lumen 239 positioned between the lumens 237 and 238. The lumens 237 are adapted to receive small size catheters 241 of the type hereinbefore described which are provided with longitudinally spaced-apart electrodes 242 on their distal extremities. The distal extremities of the catheters 241 are also provided with preformed memories so that when the distal extremities extend beyond distal extremity of the flexible elongate member 233 they will bend at a substantially right angle as shown in FIG. 17 to form what can be termed a "plaque" or in other words an arrangement in which the electrodes 242 carried by the distal extremities of the catheters 241 lie in a plane. The right angle bend of the distal extremity of the catheters 241 can be readily obtained by utilizing shape memory materials, as for example one which has the right angle memory therein but which can be straightened out when the catheter is retracted into the lumens 237 of the multi-port introducer 232. As shown in FIG. 17, the catheters 241 can be torqued so that the distal extremities are arranged in a desired pattern, as for example a circular pattern in which the distal extremities are spaced apart at substantially equal angles. Alternatively, as shown in FIG. 18 they can be positioned to extend from two sides of the distal extremity of the flexible elongate member 233 to form essentially a rectangle in plan. Such geometric arrangements are particularly desirable in mapping certain portions of the heart. As in connection with the previous embodiments if it is desired to obtain a higher resolution in a single area of the heart, the distal extremities can be torqued until they are brought in close proximity to each other to provide the high resolution mapping desired of that portion of the wall of the heart.

If after mapping has been accomplished it is desired to perform an ablation, a steerable ablation catheter of the type hereinbefore described can be introduced through the central lumen 238 or, alternatively, through a separate lumen, to accomplish the desired ablation. It should be appreciated that if desired, the ablation catheter can be in place at the time that the multi-port introducer 232 is introduced into the heart, as for example into the left ventricle of the heart.

Also in connection with the present invention it should be appreciated that means can be provided for fixing or securing the distal extremity of the multi-port introducer 232 to the wall of the heart so that the electrodes can remain stationary with respect to the wall of the heart even though the wall of the heart is moving because of beating of the heart. This can be accomplished by the use of a fixation pin 246 mounted on a flexible elongate actuation member 247 extending through the lumen 239 extending out of the distal extremity 236 of the flexible elongate member 233 to move the pin 246 into and out of engagement with the wall of the heart. Thus, the pin 246 when advanced can be utilized to retain the distal extremity 236 of the multi-port introducer 232 in the desired position on the wall of the heart during a mapping procedure or during an ablation procedure.

Figure 19:
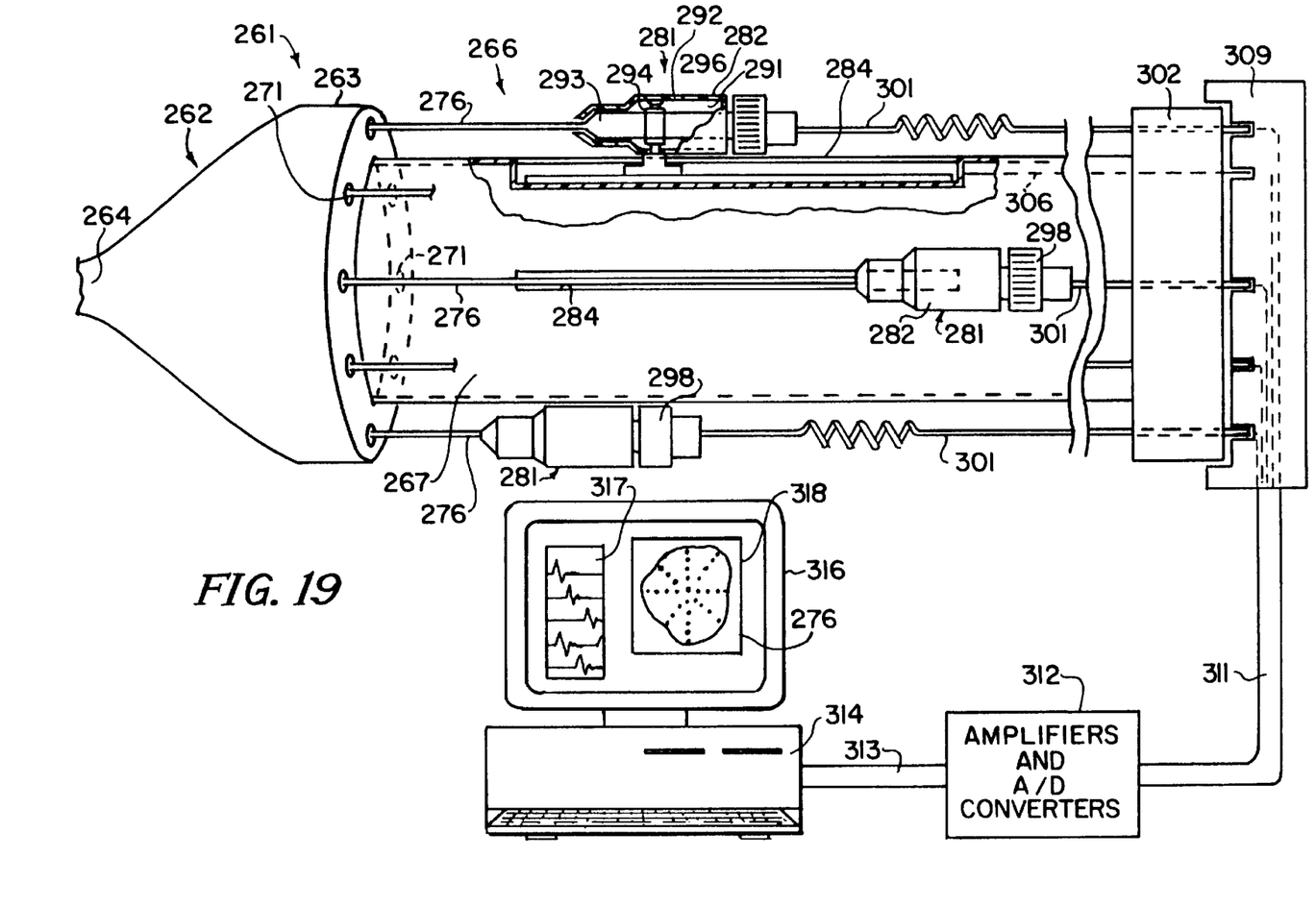
FIG. 19 is a side elevational view of an apparatus utilizing a multi-port introducer and a catheter assembly of the present invention.

In FIG. 19, there is shown an apparatus which incorporates the multi-port introducer and catheter assembly of the present invention for performing high resolution mapping. As shown in FIG. 19, this apparatus 261 is comprised of a multi-port introducer 262 which is generally of the type hereinbefore described which is provided with an enlarged hub 263 which remains outside of the body and which is coupled to a large catheter-like portion 264 of a suitable size, such as 7 or 8 French, which can be introduced into a vessel of a patient in the manner hereinbefore described. A handle assembly 266 is adapted to be engaged by the hand of a human being and is secured to the hub 263 as shown and extends proximally therefrom.

The handle assembly 266 is provided with a cylindrical housing 267 formed of a suitable material, such as plastic, and thus by way of example can have a suitable diameter as, for example, approximately one and one-half inches and can have a suitable length as for example, five to six inches. As in the previous embodiments of the multi-port introducer 262, a plurality of circumferentially spaced apart lumens 271 are provided in the hub 263 and open through the proximal extremity thereof and are spaced radially from the cylindrical housing 267 so that they are readily accessible permitting catheters 276 of the type hereinbefore described to be introduced through the lumens 271 and to extend through the large catheter-like portion 264 to enter into a chamber of the heart as hereinbefore described. Each of the catheters 276 is adapted to be rotated and is also adapted to be advanced and retracted in the manner hereinbefore described.

In conducting high resolution mapping, it has been found that it is desirable to track as precisely as possible the rotational movement of each of the catheters as well as the sliding movement of each of the catheters. Such a means has been provided as a part of the handle assembly 266 and consists of a generally cylindrical slider mechanism 281 which is provided with a housing 282 depending member 283 which extends through a longitudinally extending slot 284 provided on the cylindrical housing 267. The depending member 283 carries a slider 286 which is adapted to engage the longitudinally extending resistor 287 to form a linear potentiometer 288.

A rotary potentiometer 291 is mounted in the cylindrical housing 292 of the slider mechanism 281. The rotary potentiometer 281 includes a shaft 293 rotatably mounted in the housing 282 and which is secured to the catheter 276. The shaft 293 carries a contact member 294 which engages a cylindrical resistive element 296 secured to the interior of the cylindrical housing 282. The shaft 293 is adapted to be rotated by a knob 298 mounted on the shaft 293. The knob 298 is adapted to be engaged by the fingers of the hand carrying the handle assembly 266. Conductors (not shown) extending from the catheter 276 and from the rotary potentiometer are connected through a strain relief cable 301 and connected to an electrical connector 302 mounted on the proximal extremity of the handle of the cylindrical housing 267. Similarly, the linear potentiometer 288 is connected by a cable 306 extending interiorly of the cylindrical housing 267 and connected to the electrical connector 302.

The connector 302 is adapted to be mated with a mating connector 309 which is connected by a cable 311 to an interface box 312 containing certain conventional electronic circuitry, including amplifiers and A/D converters. The interface box 312 is connected by a cable 313 to a conventional computer 314 which has mounted thereon a video monitor 316 which by way of example can carry a pair of screens 317 and 318, one of which can be utilized to display the electrical signals received from the heart and the other of which can be utilized for displaying an isochronal map displaying the position of the catheters 276 in the chamber of the heart with their electrodes.

It should be appreciated that if desired a scale (not shown) can be provided alongside each of the linear potentiometers 288 visible from the exterior of the cylindrical housing 267 and similarly a scale (not shown) can be provided on the cylindrical housing 282 or alternatively on the knob 298. This makes it possible for the physician utilizing the handle assembly 266 to ascertain the relative positions of the catheter 276 carried by the associated slider mechanisms 281 to ascertain their extensions into the heart. Similarly, rotations associated with the knob 298 can be observed to ascertain the rotational positions of the distal extremities of the catheters 276 in a chamber of the heart. At the same time, the rotational positions given by the rotary potentiometers 291 and the linear positions given by the linear potentiometers 282 can be tracked by the computer 314 so that an approximate isochronal or isopotential map can be displayed on the screen 318.

The apparatus shown in FIG. 19 is particularly advantageous for use with patients having hearts with irregularly shaped chambers since each catheter 276 has the capability of extending a variable mount and being rotated by a variable mount it is possible for the computer 314 by ascertaining the extensions of the catheters 276 into the heart to ascertain how many electrodes on the various catheters are in engagement with the wall of the heart. The computer 314 then can make appropriate adjustments on the isochronal or isopotential images created on the screen 318. For example, for a small heart chamber it is possible that a number of the electrodes carried by the catheter might still be within the lumen of the multi-lumen catheter 264. By providing the rotary information to the computer 314 from the rotary potentiometers, it possible to ascertain the spacing between catheters in the chamber of the heart.

It should be appreciated that in the place of the foregoing it is possible for a physician to observe the positions of the rotary and linear potentiometers of the catheters with relationship to their respective scales and enter the information from the scales manually into the computer to obtain similar adjustments of the image appearing on the screen 318.

From the foregoing, it can be seen that the apparatus shown in FIG. 19 is particularly suitable for deployment in irregularly shaped chambers of hearts. It is possible to display an appropriate isochronal map even though some of the arms of the catheters may be much shorter than others in the chamber of the heart and have different numbers of electrodes in contact with the wall forming the chamber of the heart.

From the foregoing it can be seen that with the catheter assembly of the type hereinbefore described utilizing either a short or a long multi-port introducer it is possible to utilize a plurality of small diameter catheters in the same introducer through a single puncture site thereby greatly reducing the number of puncture sites normally needed for performing certain medical procedures, as for example EP studies. Although the present method has been described principally in connection with conducting electrophysiology studies and high resolution mapping, it can be seen that the concept of having a multi-port introducer with a plurality of small diameter tools, as for example catheters introduced through the multi-port introducer, other medical procedures can be performed where multiple instruments or tools are required. It also should be appreciated that although the method has been described particularly for use in the venous side of the heart, similar studies and procedures can be accomplished on other areas of the heart. It also should be appreciated that in addition to introduction through the femoral veins and arteries, other vessels of the patient can be utilized, as for example jugular veins and arteries. Also, one of the ports in the introducer may be utilized, if needed, for a saline drip/or heparin a drip. This further eliminates the necessity of one additional puncture site.

What is claimed is:

1. A method for performing a medical procedure within a patient having a vessel and a heart with a plurality of regions by the use of a multi-catheter introducer having proximal and distal extremities with at least one lumen extending from the proximal extremity to the distal extremity and a plurality in excess of two catheters for performing electrical functions adapted to be inserted through the multi-catheter introducer and having proximal and distal extremities comprising forming a single puncture site in the patient leading to the vessel, introducing the multi-port introducer through the puncture site into the vessel, introducing the plurality of catheters through the at least one lumen in the multi-catheter introducer and advancing the plurality of catheters so that the distal extremities of the plurality of catheters are disposed in the heart at the same time and manipulating the proximal extremities of the plurality of catheters to cause the distal extremities of the plurality of catheters to rotate and be advanced so that the plurality of catheters are moved into engagement with different longitudinally spaced-apart regions of the heart for simultaneously sensing electrical signals from the regions thereby permitting different electrical characteristics of said patient to be measured form a single puncture site.

2. A method as in claim 1 together with the step of moving the distal extremities of the catheters in closer proximity to each other to perform a medical procedure in a more closely spaced regions of the heart.

3. A method as in claim 1 together with the step of arranging the distal extremities of the catheters into a circular pattern in which the distal extremities are disposed radially within the circular pattern.

4. A method as in claim 1 together with the step of arranging the distal extremities of the catheters in a rectangular pattern in which the distal extremities lie parallel to each other.

5. A method as in claim 1 wherein the catheters have distal extremities with memories incorporated therein which when the distal extremities are free will assume conditions in which the distal extremities extend substantially at right angles to the axes of the catheters.

6. A method as in claim 1 wherein the manipulating step includes the step of manipulating the proximal extremities of the plurality of catheters to cause the distal extremities of the plurality of catheters to rotate and be advanced so that the plurality of catheters are moved into engagement with different chambers of the heart.

7. A method for performing a medical procedure within a patient having a vessel and a heart by use of a multi-catheter introducer having proximal and distal extremities and a plurality of catheters slidably and rotatably mounted in the multi-catheter introducer and having proximal and distal extremities and each having a plurality of spaced-apart electrodes carried by the distal extremity comprising forming a single puncture site in the patient leading to the vessel, introducing the multi-catheter introducer through the puncture site into the vessel, introducing the plurality of catheters into the multi-catheter introducer, slidably moving each of the catheters in the lumens and rotating each of the catheters so that the distal extremities are disposed in appropriate locations in the heart and ascertaining the linear and rotary positions of each of the catheters to provide information to ascertain the number of electrodes carried by the distal extremities of the catheters in contact with the patient in the heart.

8. A method as in claim 7 together with the step of utilizing the information with respect to the linear and rotary positions of each of the catheters to form an isochronal or isopotential map of the heart.

9. A method for mapping a wall of a chamber of a heart having blood therein by use of a first flexible elongate member having proximal and distal extremities and a plurality of at least three second flexible elongate members slidably and rotatably mounted in the first flexible elongate member and having proximal extremities and joined-together distal extremities and each having a plurality of longitudinally spaced-apart electrodes mounted thereon, comprising introducing the distal extremity of the first flexible elongate member into the chamber of the heart, slidably moving each of the second flexible elongate members out of the first flexible elongate member so that the second flexible elongate members form a basket-like assembly disposed in the chamber of the heart and rotating at least some of the second flexible elongate members so that the second flexible elongate members move closer together to perform fine resolution mapping of the wall of the heart.

10. A method as in claim 9 together with the step of bowing the distal extremities of the second flexible elongate members outwardly to engage the wall of the heart.

11. A method as in claim 9 wherein the slidably moving step includes individually moving each of the second flexible elongate members relative to the first flexible elongate member.

12. A method as in claim 9 wherein the rotating step includes rotating individually each of the second flexible elongate members relative to the first flexible elongate member.

* * * * *